United States Patent
Platt

(10) Patent No.: US 6,666,865 B2
(45) Date of Patent: Dec. 23, 2003

(54) SWIRLING SYSTEM FOR IONIZABLE GAS COAGULATOR

(75) Inventor: Robert C. Platt, Laguna Niguel, CA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 10/271,199

(22) Filed: Oct. 15, 2002

(65) Prior Publication Data

US 2003/0065324 A1 Apr. 3, 2003

Related U.S. Application Data

(63) Continuation of application No. 09/666,312, filed on Sep. 21, 2000, now abandoned.
(60) Provisional application No. 60/157,768, filed on Oct. 5, 1999.

(51) Int. Cl.[7] ................................. A61B 18/14
(52) U.S. Cl. ................. 606/49; 606/40; 219/121.5; 219/121.51
(58) Field of Search ................. 606/45, 46, 49, 606/41, 40; 219/121.5, 121.51

(56) References Cited

U.S. PATENT DOCUMENTS

| | | | |
|---|---|---|---|
| 2,708,933 A | 5/1955 | August | |
| 2,828,747 A | 4/1958 | August | |

(List continued on next page.)

FOREIGN PATENT DOCUMENTS

| | | |
|---|---|---|
| DE | 3710489 | 11/1987 |
| DE | 4139029 | 6/1993 |
| DE | 4326037 | 2/1995 |
| DE | 9117019.2 | 4/1995 |
| DE | 9117299 | 4/2000 |
| DE | 1984784 | 5/2000 |
| DE | 29724247 | 8/2000 |
| EP | 956827 | 11/1999 |
| FR | 1340509 | 9/1963 |
| GB | L014995 | 12/1965 |
| JP | 61-159953 | 7/1986 |
| SU | 1438745 | 11/1988 |
| WO | WO91/13593 | 9/1991 |
| WO | WO93/03678 | 3/1993 |
| WO | WO96/27337 | 9/1996 |

OTHER PUBLICATIONS

Grund et al., "Endoscopic Argon Plasma . . . Flexible Endoscopy" Surgery and Allied Technologies, No. 1, vol. 2, pp. 42–46 (Feb. 1994).

(List continued on next page.)

Primary Examiner—Lee Cohen

(57) ABSTRACT

An electrosurgical apparatus for coagulating tissue includes an elongated flexible tube having a proximal end, a distal end, and at least one aperture located therein. The proximal end of the tube receives a supply of pressurized ionizable gas and is disposed within a working channel of the endoscope. At least one electrode ionizes the gas prior to the gas exiting the aperture of the tube and an agitator causes the gas to exit the tube with predetermined flow characteristics. In one embodiment, the agitator includes a helically-shaped baffle disposed within the tube. In another embodiments, the agitator can include a rotatable baffle having apertures disposed therethrough for causing the gas to exit the tube in a swirl-like manner. Alternatively, a pair of elongated ribbons can be disposed within the tube which, under flow conditions, will cause turbulence within the gas flow.

7 Claims, 4 Drawing Sheets

U.S. PATENT DOCUMENTS

| | | |
|---|---|---|
| 3,434,476 A | 3/1969 | Shaw et al. |
| 3,569,661 A | 3/1971 | Ebeling |
| 3,692,973 A | 9/1972 | Oku et al. |
| 3,699,967 A | 10/1972 | Anderson |
| 3,832,513 A | 8/1974 | Klasson |
| 3,838,242 A | 9/1974 | Goucher |
| 3,903,891 A | 9/1975 | Brayshaw |
| 3,970,088 A | 7/1976 | Morrison |
| 3,987,795 A | 10/1976 | Morrison |
| 4,014,343 A | 3/1977 | Esty |
| 4,019,925 A | 4/1977 | Nenno et al. |
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmanesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Black et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,700,260 A | 12/1997 | Cho et al. |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,197,026 B1 | 3/2001 | Farin et al. |
| 6,213,999 B1 | 4/2001 | Platt, Jr. et al. |
| 6,264,650 B1 | 7/2001 | Hovda et al. |
| 2002/0022838 A1 | 2/2002 | Cunningham et al. |

OTHER PUBLICATIONS

Farin et al. "Technology of Argon Plasma . . . Endoscopic Applications" Endoscopic Surgery and Allied Technologies, No. 1, vol. 2, pp. 71–77 (Feb. 1994).

Brand et al. "Electrosurgical Debulking of Ovarian Cancer: A New Technique Using the Argon Beam Coagulator" Gynecologic Oncology 39.

Hernandez et al. "A Controlled Study of the Argon Beam Coagulator for Partial Nephrectomy" The Journal of Urology, vol. 143, May (J.Urol. 143: 1062–1065, 1990).

Ward et al. "A Significant New Contribution to Radical Head and Neck Surgery" Arch Otolaryngol Head Neck Surg., vol. 115, Aug. 1989, pp. 921–923.

Mark H. Mellow, "The Role of Endoscopic Laser Therapy in Gastrointestinal Neoplasms" Advanced Therapeutic Endoscopy, pp. 17–21.

Silverstein et al., "Thermal Coagulation Therapy for Upper Gastrointestinal Bleeding" Advanced Therapeutic Endoscopy, pp. 79–84.

Waye et al., "Techniques in Therapeutic Endoscopy", W.B. Saunders Company, Philadelphia, PA., pp. 1.7–1.15.

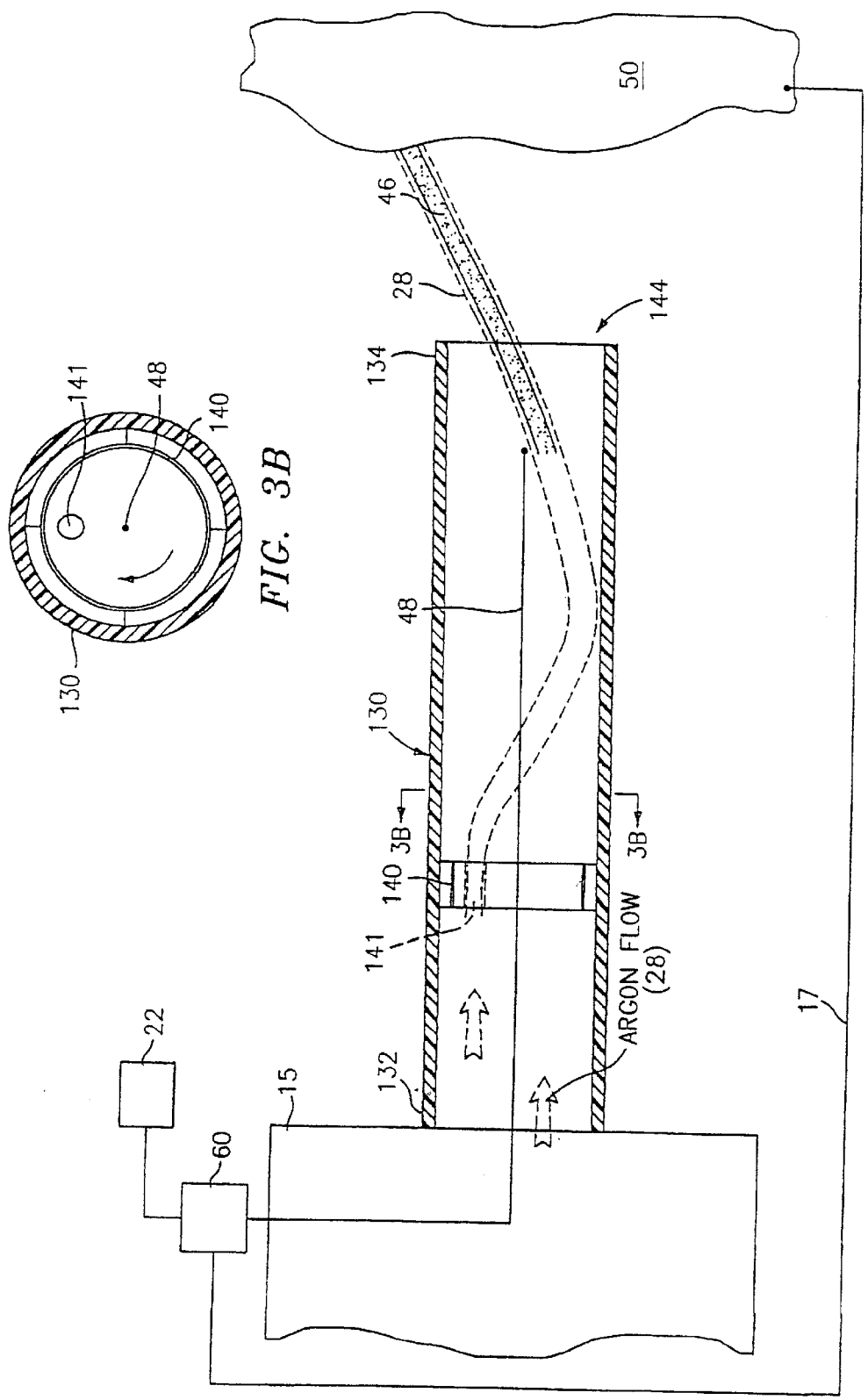

SWIRLING SYSTEM FOR IONIZABLE GAS COAGULATOR

This application is a continuation of U.S. patent application Ser. No. 09/666,312 filed on Sep. 21, 2000 now abandoned which claims the benefit to U.S. Provisional Application Serial No. 60/157,768 filed on Oct. 5, 1999.

TECHNICAL FIELD

The present disclosure relates to gas-enhanced electrosurgical devices. More particularly, the present disclosure relates to structure for aerodynamically manipulating gas flow in a gas-enhanced electrosurgical device.

BACKGROUND OF RELATED ART

Devices for arresting blood loss and coagulating tissue are well known in the art. For example, several prior art instruments employ thermic coagulation (heated probes) to arrest bleeding. However, since the probe must come into close contact with the bleeding tissue, the probe may adhere to the eschar during probe removal possibly causing repeat bleeding. Other instruments direct high frequency electric current through the tissue to stop the bleeding. Again, eschar adherence may also be a problem with these instruments. In both types of instruments, the depth of the coagulation is difficult to control.

U.S. Pat. No. 5,207,675 to Canady attempts to resolve certain of the above-noted problems with respect to the prior art by providing a tube-like coagulation instrument in which an ionizable gas is forced through the instrument and ionized by an electrode prior to the gas exiting the distal end of the instrument towards the bleeding tissue.

U.S. Pat. No. 5,720,745 to Farin et al. discloses a coagulation instrument which extends through a working channel of an endoscope and includes an electrode for ionizing a stream of ionizable gas exiting the distal end of the instrument at a rate of less than about 1 liter/minute. As explained in great detail in the Farin et al. specification, the purpose of discharging the gas at a very low flow rate is to effectively cloud the tissue area and create an ionizable gas "atmosphere" to gently coagulate the tissue. In both of the above patents, the gas flow is directed across the electrodes without manipulation.

Using these instruments to treat certain more sensitive tissue sites, may be impractical since the constant and/or direct emission of ionized gas/plasma at the tissue may cause unintended results. Moreover, simply controlling the pressure of the gas from the source may not be effective or yield a desired result.

Thus, a need also exists for the development of a new and effective instrument for controlling and manipulating the flow of gas as it flows through and exits instrument.

SUMMARY

The present disclosure relates to a gas-enhanced electrosurgical apparatus. The apparatus includes an elongated flexible tube having a proximal end and a distal end, the proximal end of the tube receives a supply of pressurized ionizable gas and may be configured to be disposed within a working channel of the endoscope. The tube includes at least one aperture and an electrode for ionizing the pressurized ionizable gas prior to the gas exiting the aperture. The apparatus also includes at least one movable incitor/agitator for controlling the flow of the gas such that the gas exits the tube with predetermined flow characteristics, e.g., swirling and/or in a more turbulent manner.

In one embodiment of the present disclosure, the agitator includes a helically-shaped baffle which causes the gas to swirl as it exits the tube. In another embodiment, the agitator includes a rotatable plenum having at least one aperture located therethrough which, under flow conditions, causes the gas to exit the tube in a swirl-like manner. In still another embodiment the agitator includes a pair of elongated ribbons supported within the tube, which, under flow conditions, flutter thus causing the gas to exit the tube in a turbulent manner.

BRIEF DESCRIPTION OF THE DRAWINGS

FIG. 3A is an enlarged, side sectional view of an alternate embodiment of the present disclosure wherein the tube includes a rotating plenum having one aperture located therein for causing the ionizable gas to exit the distal end of the tube with predetermined flow characteristics;

FIG. 3B is a cross sectional view of the FIG. 3A embodiment taken along lines 3B—3B;

DETAILED DESCRIPTION OF THE PREFERRED EMBODIMENTS

Figure 1:
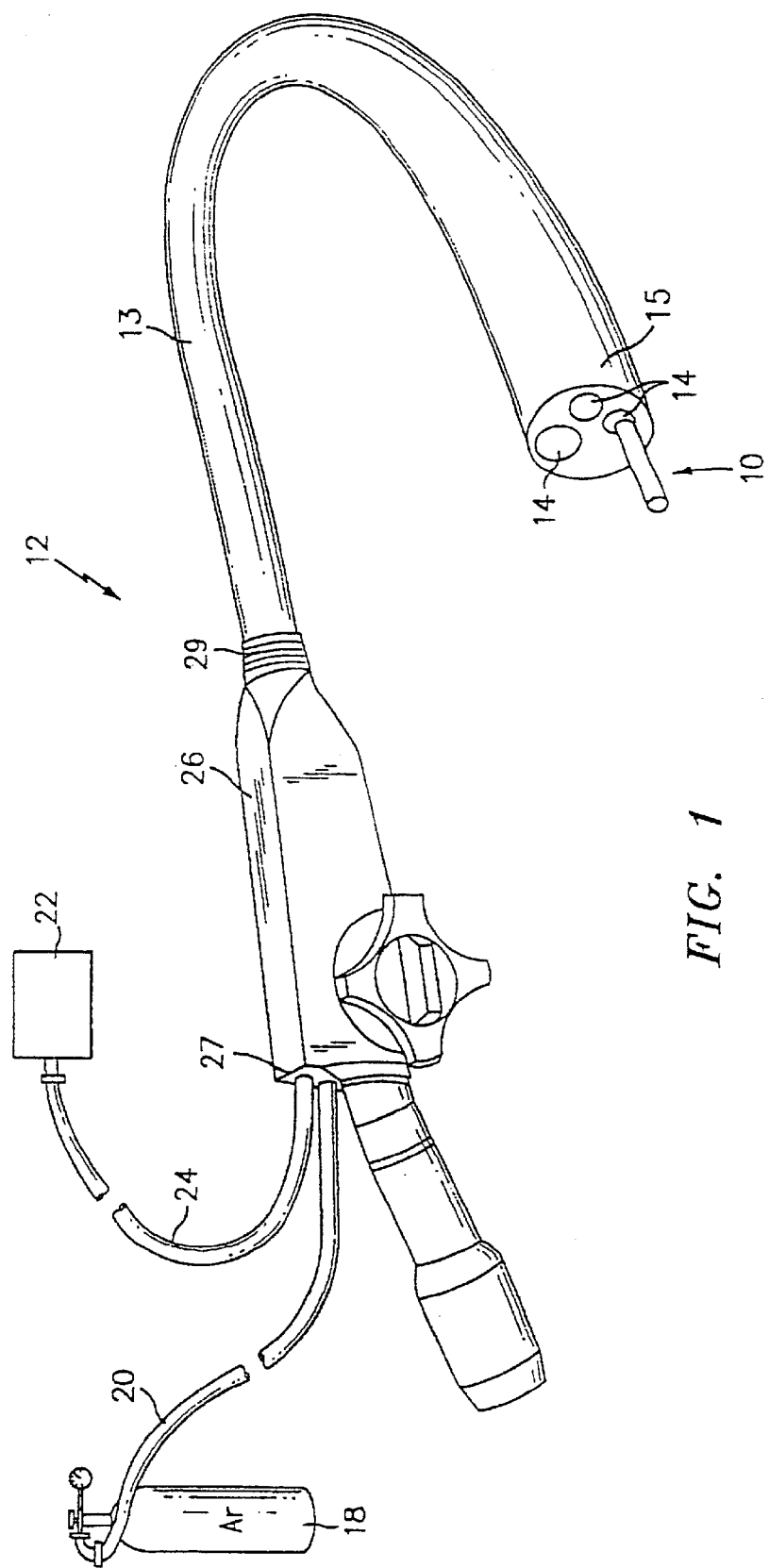
FIG. 1 is a front, perspective view of an electrosurgical instrument shown extending through a working channel of an endoscope.

Referring now to FIG. 1, a gas-enhanced side-fire tissue coagulator generally identified by reference numeral 10 is shown extending through a working channel of an endoscope 12. Preferably, the coagulator 10 can be employed with a variety of different endoscopes such as those manufactured by Olympus, Pentax and Fujinon. As such, only the basic operating features of the endoscope 12 which work in combination with the present disclosure need to be described herein.

For example, endoscope 12 includes a handpiece 26 having a proximal end 27 and a distal end 29. Preferably, the proximal end 27 is mechanically coupled to a supply 18 of pressurized ionizable gas, e.g., inert gas, by way of hose 20 and electrically coupled to an electrosurgical generator 22 by way of cable 24 to supply a source of electrosurgical energy, e.g., high frequency coagulation current, to the endoscope 12. It is envisioned that the electrosurgical generator 22 selectively controls the amount of electrosurgical energy transmitted to an electrode during a surgical procedure. It is also envisioned that the supply of pressurized ionizable gas selectively controls the rate of flow of gas greater than 1 liter per minute.

As shown in FIG. 1, a long, flexible tubular member 13 having one or more of working channels 14 located therein is mechanically coupled to the distal end 29 of the handpiece 26. Preferably, at least one of the working channels 14 is sufficiently dimensioned to receive the coagulator 10 of the present disclosure. Other working channels 14 can be utilized to receive other surgical instruments and accessories such as graspers and biopsy forceps.

Figure 2:
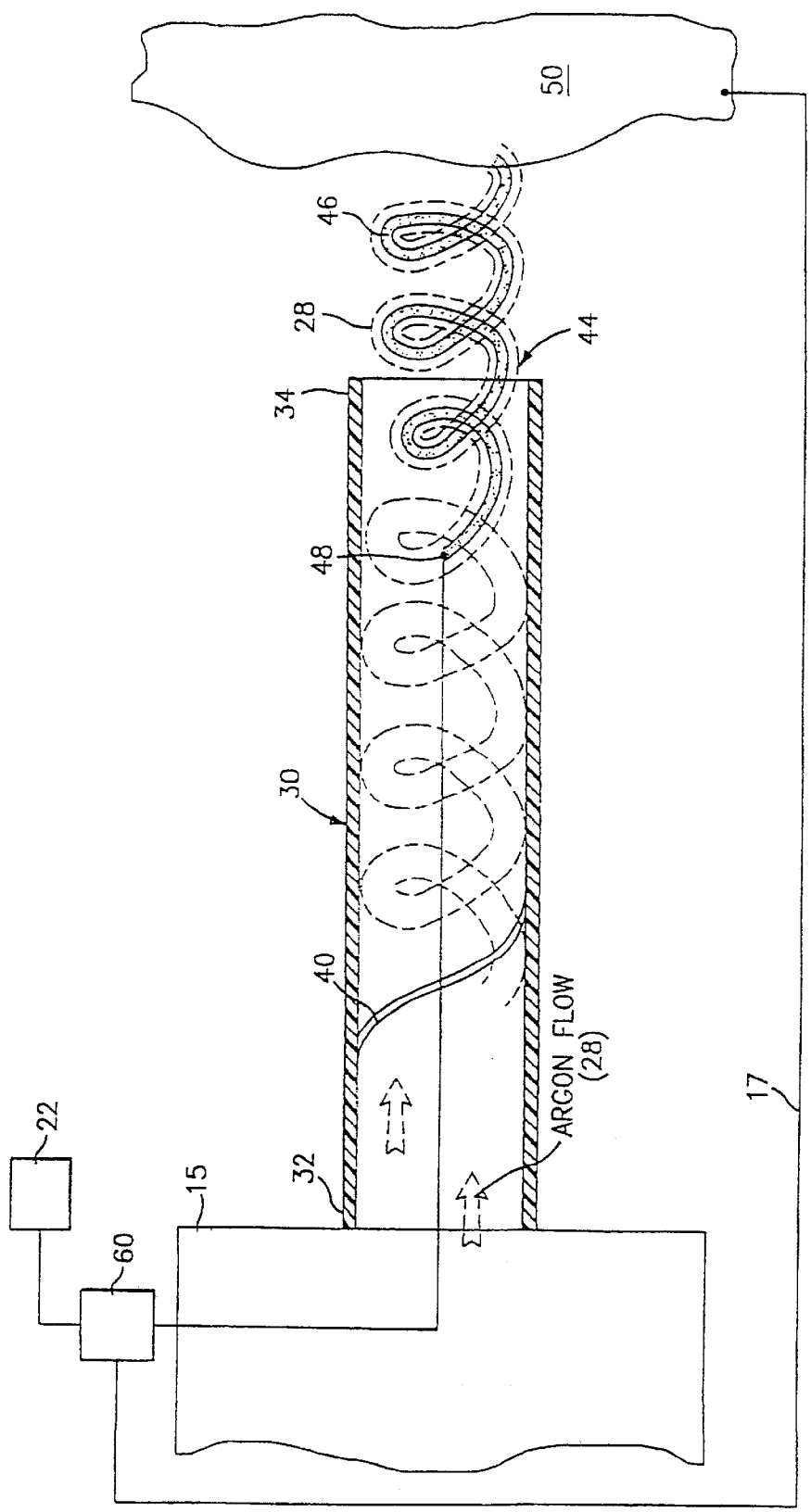
FIG. 2 is an enlarged, side sectional view of one embodiment of the present disclosure showing a helically-shaped baffle located within the tube for causing the ionizable gas to exit the distal end of the tube with predetermined flow characteristics.

Turning now to FIG. 2, one preferred embodiment of the coagulator 10 is shown therein and includes an elongated, generally flexible tube 30 having a proximal end 32 which extends through a working channel 14 of the endoscope 12 and a distal end 34 which projects outwardly from the distal end 15 of tube 13. Ionizable gas 28, e.g., argon, is supplied to the proximal end 32 of the coagulator 10 by a gas conduit (not shown) located inside tube 13. Preferably, gas 28 is supplied from source 18 to the coagulator 10 at a selectable, predetermined flow rate. Advantageously, the flow rate of the gas 28 is selectively adjustable and can easily be regulated depending upon a particular purpose or a particular surgical condition.

As mentioned above, the ionizable gas 28 is supplied under pressure to the proximal end 32 of the coagulator 10 and flows generally within the tube 30 in the direction of the arrow to exit aperture/port 44 located at the distal end 34 of tube 30. Electrode 48 discharges an electrosurgical current, e.g., radiofrequency (RF), which ionizes the gas 28 prior to the gas 28 being forced through port 44 at tissue 50. Preferably, the stream of ionized gas 46 conducts the current to the tissue 50 while effectively scattering blood away from the treatment site allowing the tissue 50 to readily coagulate and arrest bleeding.

Electrode 48 is connected by way of an electrical conduit (not shown) disposed within tubes 30 and 13 which is ultimately connected to an electrosurgical generator 22. Preferably, the electrode 48 is ring or pin-type and is spaced from the aperture 44 such that the electrode 48 cannot come into contact with the tissue 50 during the surgical procedure. In one particular embodiment of the present disclosure an electrode control mechanism 60 allows an operator to selectively adjust the amount of current flowing through the electrode 48 during surgical conditions.

Preferably, gas 28 can be controlled/manipulated such that it flows through tube 30 in a more turbulent manner. It is contemplated that many systems may be employed to cause the gas 28 to flow more or less turbulently or with other predetermined flow characteristics through tube 30. For example, a generally helically-shaped baffle 40 can be positioned within tube 30 to cause gas 28 to swirl within tube 30 prior to the gas 28 exiting aperture 44 at tissue 50.

FIGS. 3A, 3B and 4A, 4B include other flow systems for causing gas 28 to exit distal end 134, 234, respectively, with predetermined flow characteristics. More particularly, FIGS. 3A and 3B show a flow system which includes a rotatable plenum 140 having at least one aperture 141 located therethrough. Preferably, the force of the pressurized gas 28 flowing through aperture 141 causes the plenum 140 to rotate which, in turn, causes the ionizable gas 28 and plasma 46 to swirl with predetermined flow characteristics. It is envisioned that the user can control the rotational speed of the plenum 140 by varying the pressure of gas 28 flowing through tube 130, however, the rotational speed of the plenum 140 may be controlled by some other mechanism which is independent of the pressure of the gas 28, e.g., a regulator.

Figures 4A, 4B:
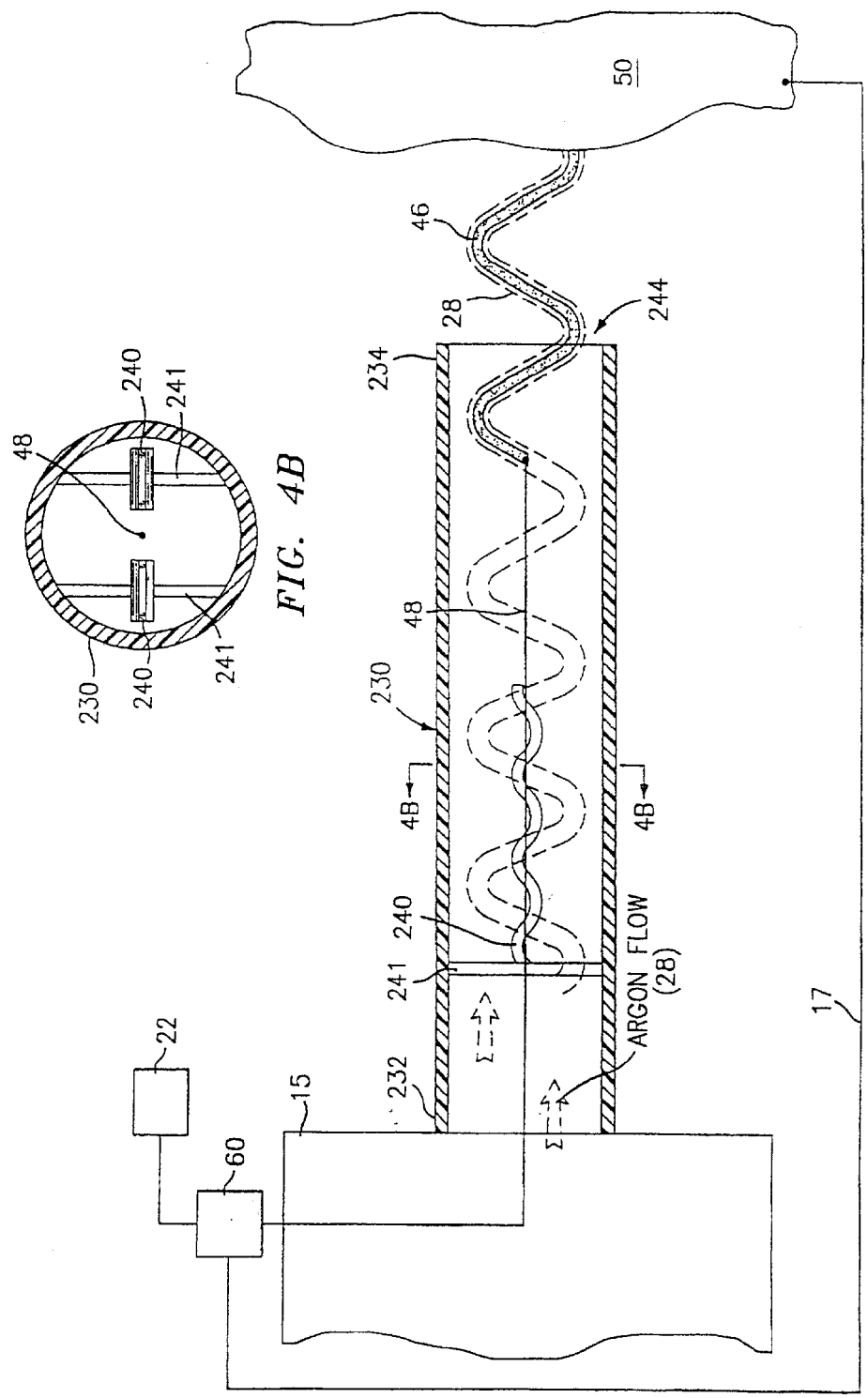
FIG. 4A is an enlarged, side sectional view of an alternate embodiment of the present disclosure wherein the tube includes a pair of elongated ribbons which, under flow conditions, cause the gas to exit the distal end of the tube with predetermined flow characteristics.
FIG. 4B is a cross sectional view of the FIG. 4A embodiment taken along lines 4B—4B.

FIGS. 4A and 4B show a flow system which includes a pair of rods 241 disposed within tube 230 for supporting a pair of elongated ribbons or flaps 240. Preferably, under flow conditions ribbons 240 attenuate/extend from rods 241 and flutter within the stream of ionizable gas 28. It is envisioned that the force of the pressurized gas 28 flowing through tube 230 causes each ribbon 240 to flutter which, in turn, causes the ionizable gas 28 and plasma 46 to move in a more turbulent manner. It is also envisioned that the rate/frequency of the flutter is directly related to the pressure of the gas 28 flowing through tube 230.

Preferably, any number of ribbons 240 can be employed to create certain flow conditions, e.g., a series of ribbons 240 can be positioned at various positions along the tube 830 to create a more turbulent gas 28 flow. Moreover, the length of each ribbon can be varied to create additional flow effects.

Although FIGS. 2–4B show the gas being emitted from the distal end of various types of coagulation devices, each of the aforedescribed flow systems may be used with other types of coagulation devices, e.g., the embodiments described in U.S. patent application Ser. No. 09/665,380 filed on Sep. 21, 2000 entitled "Articulating Ionizable Gas Coagulator" and in U.S. patent application Ser. No. 09/162,796, filed on Sep. 29, 1998 entitled "Side Fire Coagulator" the entire contents of which are both incorporated herein by reference.

From the foregoing and with reference to the various figure drawings, those skilled in the art will appreciate that not only can the coagulator 10 of the present disclosure be used to arrest bleeding tissue, but the present disclosure can also be employed for desiccating the surface tissue, eradicating cysts, forming eschars on tumors or thermically marking tissue. Those skilled in the art will also appreciate that certain modifications can also be made to the present disclosure without departing from the scope of the present disclosure.

For example, although it is preferable to utilize argon as the ionizable gas for promulgating coagulation of the tissue 50, in some cases it may be preferably to use another ionizable gas to effect the same or different result.

There have been described and illustrated herein several embodiments of a structure for aerodynamically manipulating gas flow in a gas-enhanced electrosurgical device. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical apparatus for coagulating tissue, comprising:

an elongated flexible tube having a proximal end and a distal end, the tube including at least one aperture located therein;

a source for supplying pressurized ionizable gas at a rate of greater than 1 liter per minute to the proximal end of the elongated flexible tube;

at least one electrode for ionizing pressurized ionizable gas prior to pressurized ionizable gas exiting the aperture; and a movable fluid agitator configured to impart non laminar flow characteristics to pressurized ionizable gas flowing through the flexible tube.

2. An electrosurgical apparatus according to claim 1 wherein the movable fluid agitator includes at least one baffle having at least one aperture located therethrough, the baffle being mounted for rotation within the tube.

3. An electrosurgical apparatus according to claim 2 wherein the baffle is rotatable by the flow of pressurized ionizable gas.

4. An electrosurgical apparatus according to claim 3 wherein the rotational speed of the baffle is related to the force of pressurized ionizable gas.

5. An electrosurgical apparatus according to claim 1 wherein the movable fluid agitator includes at least one support rod disposed within the tube having at least one ribbon extending therefrom.

6. An electrosurgical apparatus according to claim 5 wherein the length of each of the ribbons is varied.

7. An electrosurgical apparatus according to claim 1 wherein the movable fluid agitator includes a plurality of support rods each having at least one ribbon extending therefrom, each of the plurality of support rods being disposed at various positions within the tube.

* * * * *